(12) United States Patent
Greenberg et al.

(10) Patent No.: US 9,775,648 B2
(45) Date of Patent: Oct. 3, 2017

(54) ORTHOPEDIC IMPLANT HAVING NON-CIRCULAR CROSS SECTION AND METHOD OF USE THEREOF

(71) Applicants: Louis E. Greenberg, Niwot, CO (US); Kevin P. McAbee, Denver, CO (US); William C. Caile, Denver, CO (US); Jackson L. White, Denver, CO (US)

(72) Inventors: Louis E. Greenberg, Niwot, CO (US); Kevin P. McAbee, Denver, CO (US); William C. Caile, Denver, CO (US); Jackson L. White, Denver, CO (US)

( * ) Notice: Subject to any disclaimer, the term of this patent is extended or adjusted under 35 U.S.C. 154(b) by 452 days.

(21) Appl. No.: 14/078,282

(22) Filed: Nov. 12, 2013

(65) Prior Publication Data

US 2014/0222087 A1    Aug. 7, 2014

Related U.S. Application Data

(60) Provisional application No. 61/725,580, filed on Nov. 13, 2012.

(51) Int. Cl.
*A61B 17/68* (2006.01)
*A61B 17/86* (2006.01)

(52) U.S. Cl.
CPC ............ *A61B 17/683* (2013.01); *A61B 17/86* (2013.01); *A61B 17/8695* (2013.01)

(58) Field of Classification Search
CPC ....... A61B 17/84; A61B 17/844; A61B 17/86; A61B 17/8606; A61B 17/861;
(Continued)

(56) References Cited

U.S. PATENT DOCUMENTS

| | | | |
|---|---|---|---|
| 2,489,870 A | * | 11/1949 | Dzus .................... A61B 17/683 411/339 |
| 3,783,860 A | | 1/1974 | Burstein et al. |

(Continued)

FOREIGN PATENT DOCUMENTS

WO          97/22301         6/1997

OTHER PUBLICATIONS

International Search Report, International Searching Authority, PCT/US13/69727, dated Jan. 30, 2014, pp. 1-28.

*Primary Examiner* — Eric S Gibson
(74) *Attorney, Agent, or Firm* — Samuel M. Freund; Cochran Freund & Young LLC

(57) ABSTRACT

Orthopedic implants capable of compressing adjacent bone segments into which they are inserted, effective for the fusion, management and repair of bone joints and bone fractures, and methods for their installation, are described. One embodiment of such implants includes an elongated shaft coated to encourage bony in-growth, having a non-round cross section, and a flange at one end, which is laterally inserted into a preformed insertion path formed in adjacent bone segments traversing a joint or fracture location, to the point where further insertion is blocked by the flange intersecting one of the bone segments. The other end of the shaft may have a portion of male thread protruding out of the insertion path in the second of the bone fragments and adapted to be mated to a fastener having female thread. When the fastener is tightened against the outside of the second bone segment, perhaps using a washer, the joint or fracture is compressed and stabilized resulting in an effective fusion of the joint or fracture when the bone secures itself in the insertion path to the shaft's bony in-growth surfaces on both sides of the joint or fracture line.

14 Claims, 5 Drawing Sheets

(58) Field of Classification Search
CPC .............. A61B 17/8615; A61B 17/862; A61B 17/8625; A61B 17/863; A61B 17/8635; A61B 17/864; A61B 17/8645; A61B 17/866; A61B 17/8665; A61B 17/8685; A61B 17/8695; A61B 2017/8655; A61B 2017/867; F16B 35/041
USPC ......................................................... 411/424
See application file for complete search history.

(56) References Cited

U.S. PATENT DOCUMENTS

| | | | |
|---|---|---|---|
| 3,977,398 A | 8/1976 | Burstein | |
| 4,456,005 A * | 6/1984 | Lichty | A61B 17/8685 606/315 |
| 4,854,114 A * | 8/1989 | Speck | A01D 34/13 411/169 |
| 4,875,474 A | 10/1989 | Border | |
| 5,100,405 A | 3/1992 | McLaren | |
| 5,217,462 A * | 6/1993 | Asnis | A61B 17/74 606/105 |
| 5,498,265 A * | 3/1996 | Asnis | A61B 17/74 606/315 |
| 5,919,194 A | 7/1999 | Anderson | |
| 5,968,047 A | 10/1999 | Reed | |
| 5,989,255 A * | 11/1999 | Pepper | A61B 17/8685 606/306 |
| 6,053,916 A * | 4/2000 | Moore | A61F 2/30988 606/86 R |
| 6,077,264 A * | 6/2000 | Chemello | A61B 17/7225 606/62 |
| 6,302,887 B1 * | 10/2001 | Spranza | A61B 17/683 411/338 |
| 6,511,481 B2 * | 1/2003 | von Hoffmann | A61B 17/68 606/60 |
| 6,887,243 B2 * | 5/2005 | Culbert | A61B 17/68 606/65 |
| 6,902,567 B2 * | 6/2005 | Del Medico | A61B 17/746 411/271 |
| 6,951,561 B2 * | 10/2005 | Warren | A61B 17/68 606/328 |
| 7,922,765 B2 * | 4/2011 | Reiley | A61B 17/1615 606/279 |
| 7,998,176 B2 * | 8/2011 | Culbert | A61B 17/1671 606/247 |
| 8,202,305 B2 * | 6/2012 | Reiley | A61B 17/1615 606/105 |
| 8,262,706 B2 * | 9/2012 | Olms | A61B 17/683 606/280 |
| 8,317,845 B2 * | 11/2012 | Stinnette | A61B 17/8028 606/264 |
| 8,388,667 B2 * | 3/2013 | Reiley | A61B 17/68 606/300 |
| 8,414,648 B2 * | 4/2013 | Reiley | A61B 17/1615 606/246 |
| 8,425,570 B2 * | 4/2013 | Reiley | A61B 17/1615 128/898 |
| 8,444,693 B2 * | 5/2013 | Reiley | A61B 17/1615 606/246 |
| 8,470,004 B2 * | 6/2013 | Reiley | A61B 17/8685 606/246 |
| 8,585,744 B2 * | 11/2013 | Duggal | A61B 17/683 606/301 |
| 8,945,193 B2 * | 2/2015 | Kirschman | A61B 17/7064 606/304 |
| 8,986,348 B2 * | 3/2015 | Reiley | A61B 17/1615 606/279 |
| 8,992,587 B2 * | 3/2015 | Kirschman | A61B 17/7064 606/305 |
| 9,011,501 B2 * | 4/2015 | Mikhail | A61B 17/683 606/305 |
| 2001/0049529 A1 * | 12/2001 | Cachia | A61B 17/68 606/301 |
| 2003/0097132 A1 * | 5/2003 | Padget | A61B 17/683 606/65 |
| 2004/0127906 A1 * | 7/2004 | Culbert | A61B 17/7064 606/247 |
| 2006/0036251 A1 * | 2/2006 | Reiley | A61B 17/1615 606/301 |
| 2006/0041261 A1 * | 2/2006 | Osypka | A61B 17/8685 606/308 |
| 2006/0079895 A1 * | 4/2006 | McLeer | A61B 17/863 606/279 |
| 2006/0089647 A1 * | 4/2006 | Culbert | A61B 17/68 606/65 |
| 2008/0125814 A1 * | 5/2008 | Yuan | A61B 17/1757 606/247 |
| 2009/0099610 A1 | 4/2009 | Johnson et al. | |
| 2009/0157119 A1 * | 6/2009 | Hale | A61B 17/1659 606/247 |
| 2009/0248089 A1 * | 10/2009 | Jacofsky | A61B 17/686 606/311 |
| 2009/0259261 A1 * | 10/2009 | Reiley | A61B 17/8897 606/329 |
| 2010/0204700 A1 | 8/2010 | Falahee | |
| 2010/0318085 A1 * | 12/2010 | Austin | A61B 17/0642 606/62 |
| 2011/0087294 A1 * | 4/2011 | Reiley | A61B 17/1615 606/279 |
| 2011/0087296 A1 * | 4/2011 | Reiley | A61B 17/1659 606/303 |
| 2011/0118841 A1 * | 5/2011 | Reiley | A61B 17/1615 623/17.11 |
| 2011/0137356 A1 * | 6/2011 | Kollmer | A61B 17/1767 606/324 |
| 2011/0166608 A1 * | 7/2011 | Duggal | A61B 17/683 606/320 |
| 2011/0190829 A1 * | 8/2011 | Duggal | A61B 17/683 606/301 |
| 2012/0191191 A1 * | 7/2012 | Trieu | A61B 17/683 623/17.11 |
| 2014/0031934 A1 * | 1/2014 | Trieu | A61F 2/30988 623/17.11 |
| 2014/0066991 A1 * | 3/2014 | Marik | A61B 17/7032 606/279 |
| 2014/0222087 A1 * | 8/2014 | Greenberg | A61B 17/8695 606/301 |
| 2014/0343616 A1 * | 11/2014 | Sellers | A61B 17/864 606/304 |
| 2014/0350608 A1 * | 11/2014 | Goel | A61B 17/7064 606/279 |

\* cited by examiner

ORTHOPEDIC IMPLANT HAVING NON-CIRCULAR CROSS SECTION AND METHOD OF USE THEREOF

CROSS-REFERENCE TO RELATED APPLICATIONS

The present application claims the benefit of U.S. Provisional Patent Application No. 61/725,580 for "Orthopedic Implant Having Non-Circular Cross Section And Method Of Use Thereof," which was filed on Nov. 13, 2012, the entire content of which is hereby specifically incorporated by reference herein for all that it discloses and teaches.

FIELD OF THE INVENTION

The present invention relates generally to orthopedic devices for fixation or fusion of bones and, more particularly, to the use of bony in-growth or through-growth coated orthopedic implants for securing bone segments against one another, for example, for fixing bone fractures or for fusing bones.

BACKGROUND OF THE INVENTION

There are numerous bone fixation/fusion systems, devices and associated methods for stabilizing adjacent bone segments, thereby enhancing the healing of fractures and/or promoting union of joints being fused together. Adjacent bone segments may include parts of the same bone that have been fractured, or two or more individual bones separated by a space or joint. Examples of orthopedic fixation/fusion devices include bone screws, metal pins, intramedullary implants, and compressive implants. A compressive implant may include a body inserted into a first and a second bone segment spanning the fracture line or joint between the two bones, with one end anchored to an interior region of the second bone segment, while the other end is anchored to a location outside of the first bone. The two anchors are used to place the body in compression which in turn compresses and fixes the bone segments relative to the fracture line or joint.

As stated, bone fixation/fusion systems, with the exception of cable-type orthopedic implants, which cannot provide rotational stabilization, are generally anchored to the cancellous bone material in the interior of the bone. This material is soft and spongy and has inferior holding capability when compared to the exterior, cortical bone portions. The forces imposed on such devices may exceed the holding capability of the cancellous bone, and may result in implant failure.

SUMMARY OF THE INVENTION

Embodiments of the present invention overcome the disadvantages and limitations of the prior art by providing an orthopedic implant for securing bone segments against one another having anchor locations on exterior surfaces of the bones.

Another object of embodiments of the present invention is to provide an orthopedic implant for securing bone segments against one another and for compressing and stabilizing the bones having anchor locations on exterior surfaces of the bones, wherein effective bone fusion occurs.

Yet another object of embodiments of the present invention is to provide a method for preparing an insertion path into adjacent bone segments adapted for the lateral insertion of an elongated orthopedic implant for securing the bone segments against one another, while maintaining the alignment of the insertion through the first and second bone segments.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purposes of the present invention, as embodied and broadly described herein, the orthopedic implant for securing bone segments against one another, hereof, includes: an elongated shaft having a non-circular cross section, an axis, a first end, a second end, an external surface, and a male threaded portion along the axis terminating at the first end; a flange affixed to the second end of the shaft; and an internally threaded fastener adapted for being threaded onto the threaded end of the shaft.

In another aspect of the present invention and in accordance with its objects and purposes, the orthopedic implant for securing bone segments against one another, hereof, includes: an elongated shaft having a non-circular cross section, an axis, a first end, a second end, an external surface, and a female threaded portion along the axis terminating at the first end; a flange affixed to the second end of the shaft; and a fastener having a male threaded portion adapted for being threaded into the female threaded portion of the shaft.

In yet another aspect of the present invention and in accordance with its objects and purposes, the method for installing an elongated orthopedic implant for securing adjacent first and second bone segments, hereof, includes: drilling a hole through the first and second bone segments spanning a fracture line or joint between the first and second bone segments using a drill bit; driving the drill bit out of the hole in a direction opposite to the direction of drilling using a broach having the same cross section as the implant, wherein the chisel points of the broach are in contact with the cutting tip of the drill; whereby an insertion path for the implant is formed; and driving the broach out of the insertion path by inserting the implant into the insertion path in the direction opposite to the broaching direction.

In still another aspect of the present invention and in accordance with its objects and purposes, the method for compressing adjacent first and second bone segments, hereof, includes: preparing an insertion path through the first and second bone segments spanning a fracture line or joint between the first and second bone segments; providing an elongated implant having an axis along the long dimension thereof, an outer surface, a first end and a second end; affixing a first flange member to the first end of the implant; inserting the second end of the implant into the insertion path; affixing a second flange member to the second end of the implant after said step of inserting the second end of the implant into the insertion path; and adjusting the distance between the first flange member and the second flange member; whereby the adjacent bone segments are compressed along the fracture line or joint therebetween.

Benefits and advantages of embodiments of the present invention include, but are not limited to, providing an orthopedic implant: (1) capable of compressing adjacent bones along a fracture line or a joint therebetween using external portions of these bones with no reliance on the soft, spongy materials interior thereto; (2) effective for promoting joint fusion without requiring the bony surfaces on both sides of the joint to be surgically abraded and compressed with bone screws and, as anticipated by the present inventors, without requiring lengthy healing periods; (3) effective for immobilizing the joint, thereby eliminating or minimizing the need for supplemental casting of the joint or use of other immobilization hardware during healing, which is important for veterinary applications where casting may be difficult; and (4) effective for stabilizing the bones during the bony ingrowth healing phase.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Briefly, embodiments of the present invention include titanium orthopedic implants, coated to encourage bony in-growth or through-growth, for the fusion, management and repair of bone joints and bone fractures. Examples of applications of such implants are femoral stems for total hip replacements, surfaces on the tibial and femoral sides of total knee implants and surfaces on the tibial and talar sides of total ankle implants. One embodiment of such implants includes an elongated shaft coated to encourage bony in-growth, having a non-round cross section (triangular, as an example), and a flange at one end (the proximal end), which is laterally inserted into a preformed insertion path formed in adjacent bone segments traversing a joint or fracture location, to the point where further insertion is blocked by the flange intersecting one of the bone segments. The other end of the shaft (the distal end) may have a portion of male thread protruding out of the insertion path in the second of the bone fragments adapted to be mated to a fastener having female thread. When the fastener is tightened against the outside of the second bone segment, perhaps using a washer, the joint or fracture is compressed and stabilized resulting in an effective fusion of the joint or fracture when the bone secures itself in the insertion path to the shaft's bony in-growth surfaces on both sides of the joint or fracture line.

Figure 1:
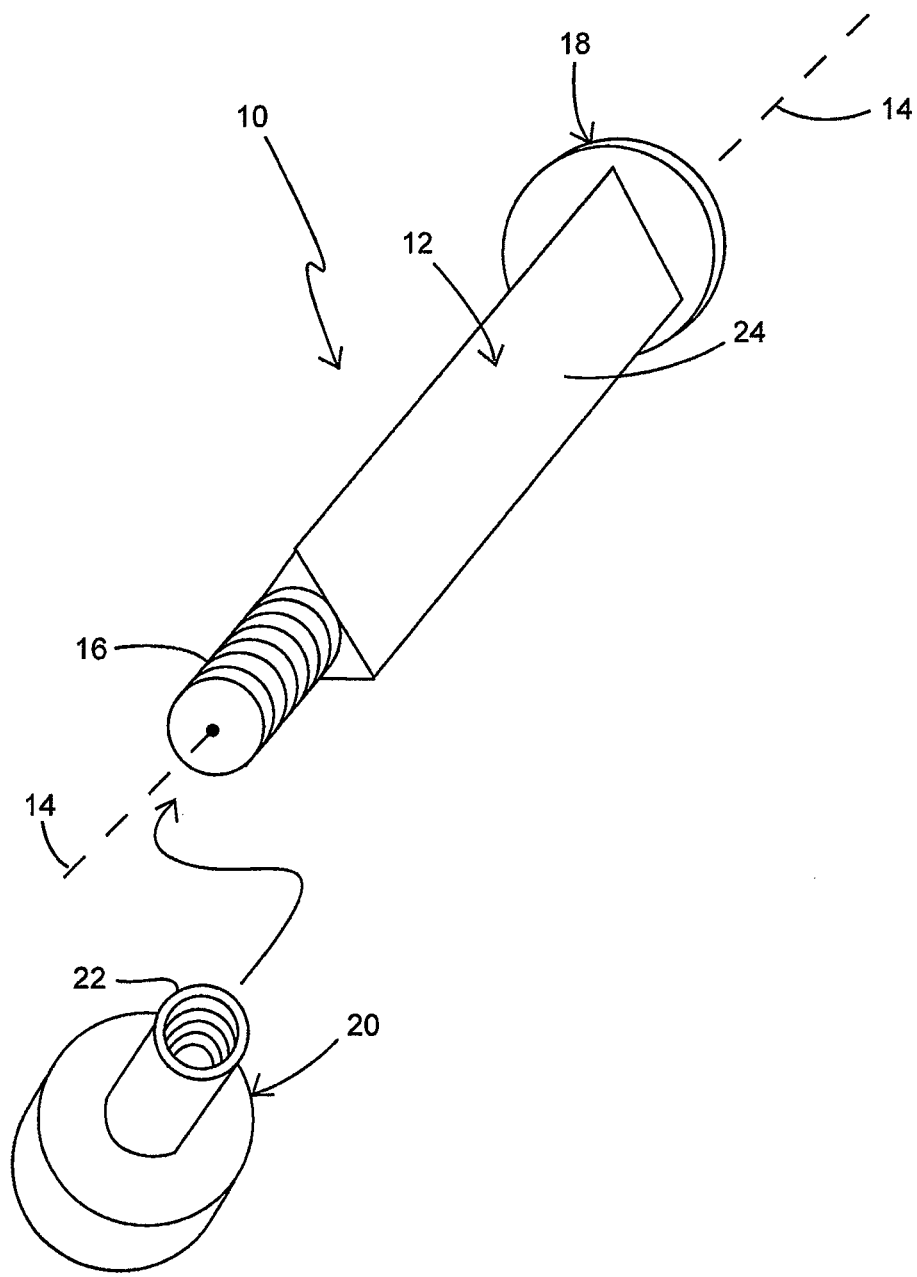
FIG. 1 is schematic representation of an exploded perspective view of an embodiment of the orthopedic implant of the present invention illustrating an elongated shaft having a triangular cross section, a flange at one end and a threaded portion at the other end, and a fastener having internal threads.

Reference will now be made in detail to the present embodiments of the invention, examples of which are illustrated in the accompanying drawings. In the FIGURES, similar or identical structure will be identified using identical reference characters. It will be understood that the FIGURES are for the purpose of describing particular embodiments of the invention and are not intended to limit the invention thereto. Turning first to FIG. 1, shown is a schematic representation of an exploded perspective view of an embodiment, 10, of the orthopedic implant of the present invention illustrating elongated shaft, 12, having non-circular cross section, here illustrated as having triangular cross section, having axis, 14, male threaded portion 16, at one end, flange, 18, attached to the other end, and fastener, 20, having internal threads, 22, adapted for being screwed onto threaded portion 16 of shaft 12. Shaft 12, flange 18 and fastener 20, may be fabricated from titanium, and flange 18 may be integrally formed with shaft 12 or attached thereto, as will be discussed in more detail hereinbelow. Surface, 24, of shaft 12 may be treated with bony in-growth or bony through-growth material as is well-known in the art. Clearly, other non-circular shapes may be anticipated for shaft 12, examples being: square, rectangular, oval, etc., as will be explained in more detail hereinbelow. Shafts may be supplied in various lengths and cross section sizes depending on their intended use.

Figure 2:
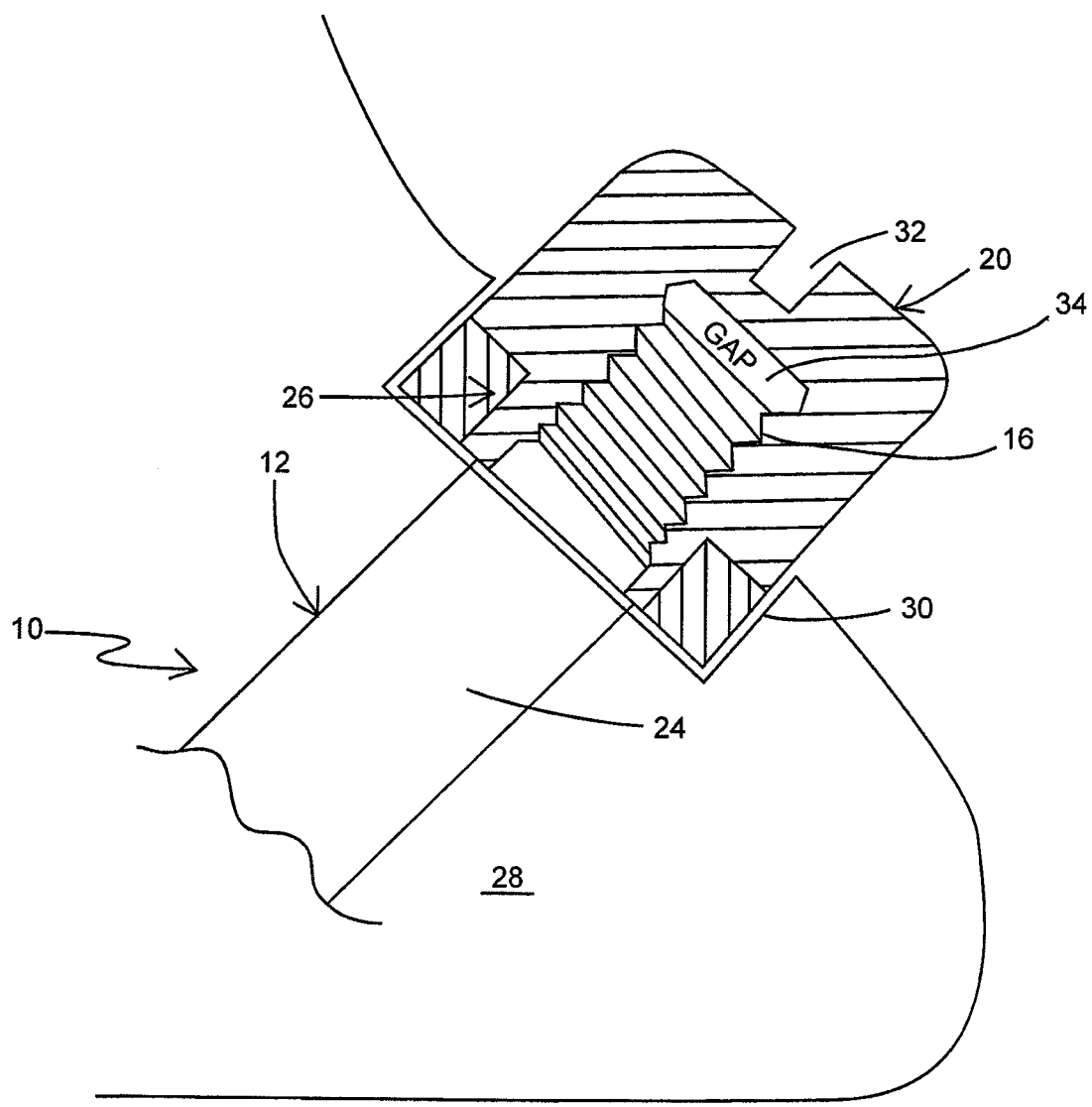
FIG. 2 is schematic representation of a perspective side view of an embodiment of the orthopedic implant of the present invention shown in FIG. 1, hereof, illustrating the internally threaded fastener threaded onto the threaded portion of the elongated shaft with a washer separating the bone from the internally threaded fastener.

FIG. 2 is schematic representation of a perspective side view of an embodiment of orthopedic implant 10 of the present invention shown in FIG. 1, hereof, illustrating internally threaded fastener 20 threaded onto threaded portion 16 of elongated shaft 12 with washer, 26, separating bone, 28, from threaded fastener 20. Bone 28 is shown to be counter bored, 30, to reduce the profile of fastener 20 extending away from bone 28, which may be necessary in situations where space is limited. Slot, 32, is shown in fastener 30 to permit tightening thereof onto thread 16 using a bladed screw driver. Holes adapted to be used with Allen or Torx wrenches, or crossed slots for use with Phillips screw drivers may also be used. Other exterior shapes for fastener 20 may permit wrenches such as box or open-ended wrenches to be employed. Gap, 34, is included to permit full tightening of fastener 20.

Figure 3:
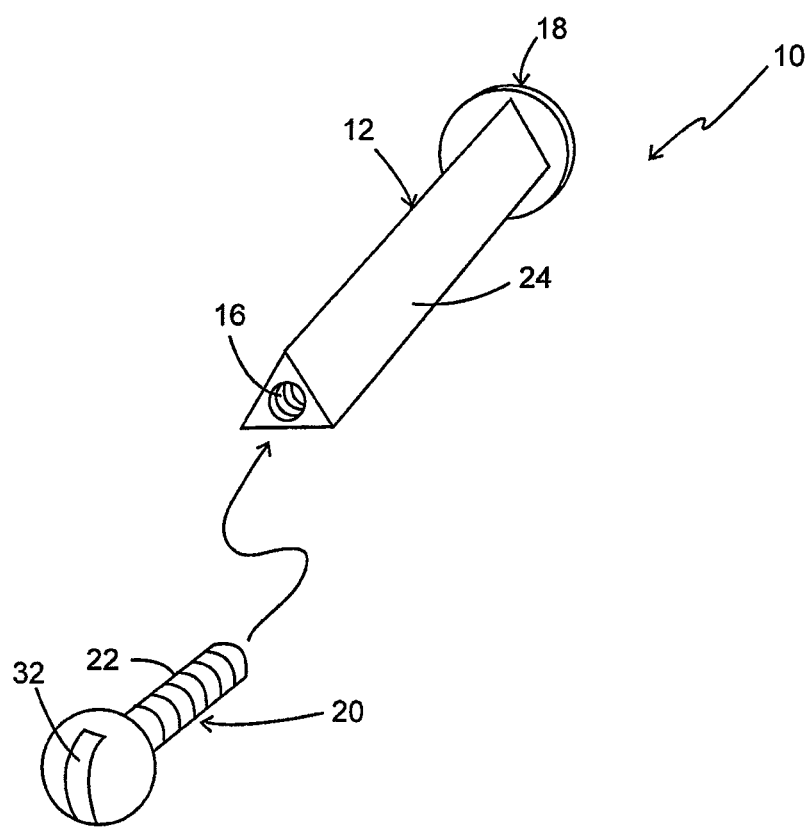
FIG. 3 is schematic representation of an exploded perspective view of a second embodiment of the orthopedic implant of the present invention illustrating an internally threaded elongated shaft having a triangular cross section, and a fastener having male threads.

FIG. 3 is schematic representation of an exploded perspective view of a second embodiment of orthopedic implant 10 of the present invention illustrating elongated shaft 12 shown as having a triangular cross section, flange 18 at the proximal end thereof, and an internal threaded portion 16 at the distal end. Associated fastener 20 has male threads 22. Surface 24 of shaft 12 may be treated with bony in-growth or bony through-growth material as is well-known in the art. Slot 32 is shown in fastener 20 to permit tightening thereof onto thread 16 using a bladed screw driver.

Figure 4:
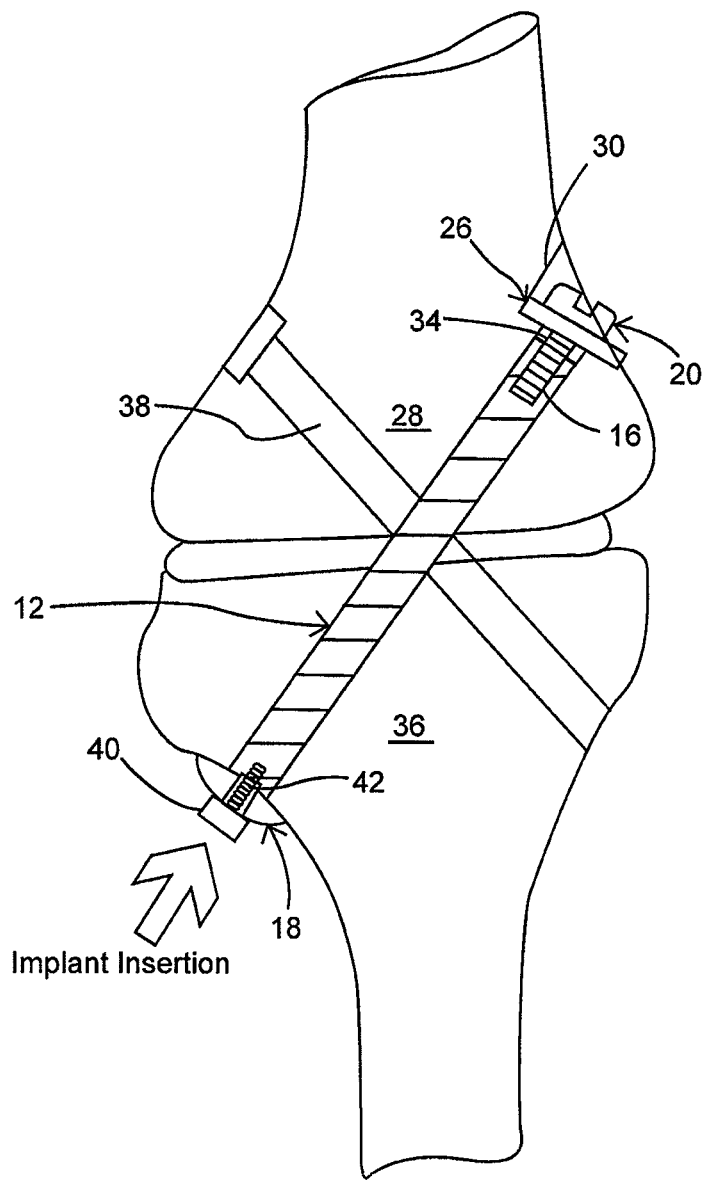
FIG. 4 is schematic representation of the use of the embodiment of the invention shown in FIG. 3 hereof for stabilizing and fusing a joint, there being more than one implant required in some situations.

FIG. 4 is schematic representation of the use of the embodiment of the invention shown in FIG. 3 hereof for stabilizing and fusing a joint, there being more than one implant required in some situations. Implant 10 is illustrated connecting bone segments 28 and, 36, while insertion path, 38, has been prepared for lateral insertion of another implant 10. Generally, the implants will be installed either diagonal or parallel to the bones. FIG. 4 also shows flange 18 as being affixed to shaft by screw, 40, which is screwed into threads, 42, formed in the proximal end of shaft 12, as opposed to being integrally formed therewith.

As stated, it is anticipated that the effective joint fusion will occur more quickly than that for a traditional more invasive joint fusion, wherein the bony surfaces on both sides of the joint are surgically abraded and compressed with bone screws. With the present bony in-growth implants, effective joint fusion is anticipated to occur in about six weeks, while with the traditional technique, fusion doesn't become effective for eight to twelve weeks. The present shaft/fastener system compresses and immobilizes the joint and eliminates or minimizes the need for supplemental casting of the joint during healing, which is an especially useful feature for veterinary applications since casting is always a problem with animals. The shaft, not being round, cannot rotate in the insertion path, which stabilizes the bones during the bony in-growth phase of healing. The combination of an anti-rotation triangular cross section, for example, and the compressive action of the shaft/fastener system constrains all the potential modes of translational and rotational motion which would otherwise inhibit bone fusion to the shaft and subsequent healing.

Bone fractures may be similarly treated. A bony in-growth treated shaft having triangular cross section, for example, is inserted into a pre-drilled and broached bone traversing the fracture and is mated to a fastener on the distal end. When the fastener is tightened to the shaft it compresses the bone fracture, resulting in an effective fusion of the bones at the fracture line when the bone secures itself to the implant's bony in-growth surfaces on both sides of the fracture. Again, the fracture is anticipated to be fused to the shaft on both sides of the fracture line in about six weeks. Additionally, after the traditional eight to twelve weeks, the bone fuses to itself, further strengthening the fracture site.

The bone joint or bone fracture is prepared by first drilling a conventional round hole across the bone joint or bone fracture and then modifying the round hole to be more appropriate for the particular implant to be installed. For example, a triangular cross section broach might be used to modify the round hole to better accommodate a triangular cross section shaft.

Figure 5:
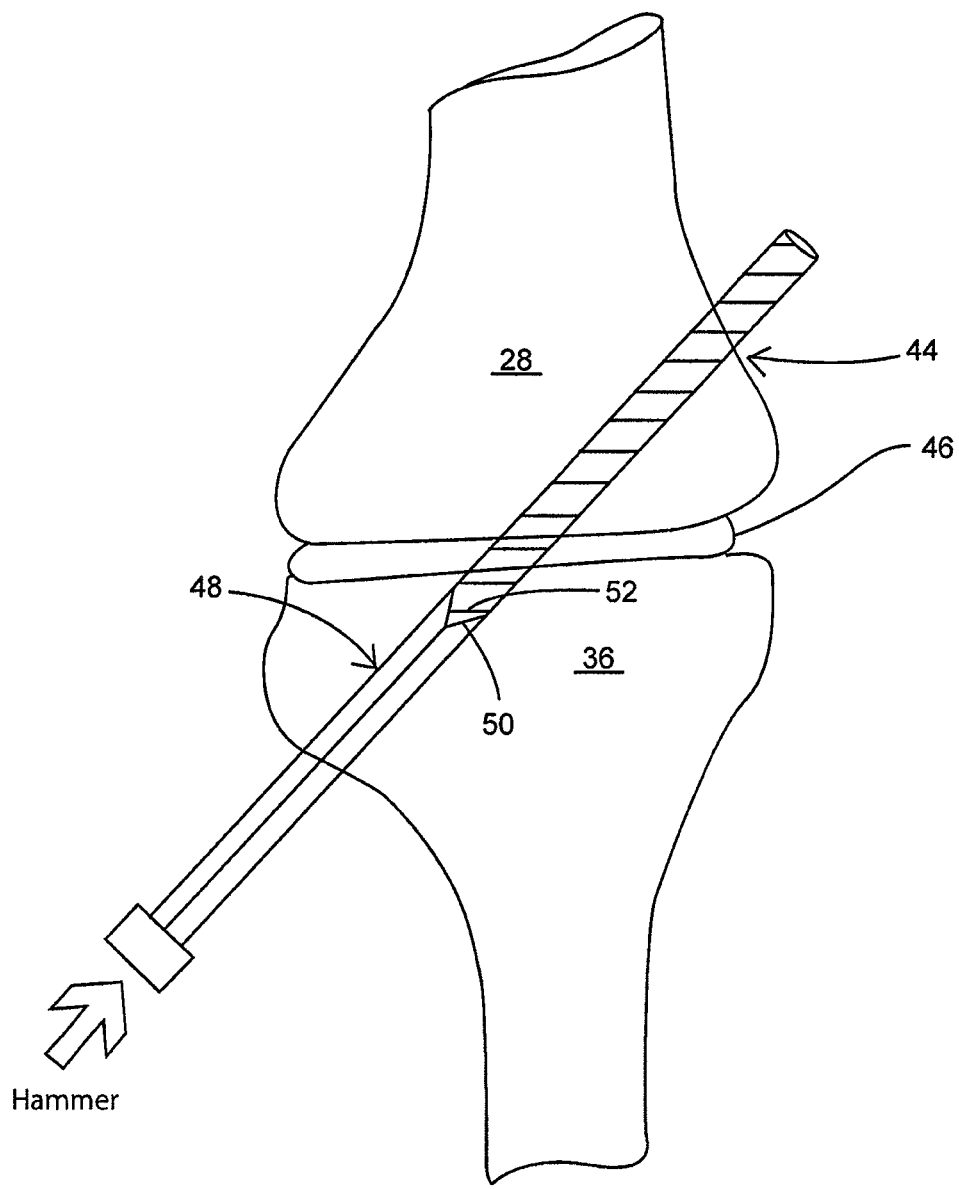
FIG. 5 is a schematic representation of a method for installing the present orthopedic implant for stabilizing or fusing a joint.

FIG. 5 is a schematic representation of a method for installing the present orthopedic implant for stabilizing or fusing a joint. Drill bit, 44, is used to drill a round hole having a diameter smaller than the implant shaft, into bone 28, through bone joint or bone fracture, 46, and out through bone 36. Drill bit 44 is subsequently detached from the driving drill (not shown in FIG. 5). Then, an appropriately shaped broach, 48, having concave chisel points, 50, are butted against and capture cutting tip, 52; of the drill broach 48 is then driven against the drill, forcing it back out of the drilled hole, while simultaneously modifying the shape of the drilled hole to fit the chosen geometry (triangular, in this example) of implant 10. In a similar manner, implant 10 (not shown in FIG. 5) is driven against now protruding broach 48 and into the broached hole, driving the broach out through bone 28, and properly placing implant 10 in the broached hole spanning bone joint or bone fracture 46. Securing fastener 20 (nut, screw, etc.) may then be attached to the distal end of implant 10 and tightened to compress bone joint or bone fracture 46 to achieve the desired surgical affect. A direct consequence of the above-identified procedure is to ensure that the initial alignment of bones segments 28 and 36 established by drill bit 44 is maintained. With broach 48 driving out drill bit 44 and, in turn being driven out by implant 10, implant 10 is properly installed in the original drilled hole, and the original hole alignment is not lost.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An orthopedic implant for securing bone segments against one another, comprising:
    an elongated monolithic shaft having a longitudinal axis, a non-circular transverse cross section perpendicular to the longitudinal axis, a first end, a second end, an external surface, and a male threaded portion along the axis terminating at the first end;
    a flange disposed on the second end of said shaft; and
    an internally threaded fastener adapted for being threaded onto the threaded end of said shaft,
    wherein the external surface of said shaft is treated to provide a bony in-growth or bony through-growth property thereto.

2. The implant of claim 1, wherein the non-circular cross section is chosen from triangular, square, rectangular, and oval shapes.

3. The implant of claim 1, wherein said shaft comprises titanium.

4. The implant of claim 1, wherein said flange is affixed to said shaft.

5. The implant of claim 1, wherein said flange is integrally formed with said shaft.

6. The implant of claim 1, further comprising a washer having a hole adapted to fit over the threaded portion of said shaft.

7. The implant of claim 1, further comprising means for rotating said fastener onto the threaded portion of said shaft.

8. An orthopedic implant for securing bone segments against one another, comprising:
    an elongated monolithic shaft having a longitudinal axis, a non-circular transverse cross section perpendicular to the longitudinal axis, a first end, a second end, an external surface, and a female threaded portion along the axis terminating at the first end;
    a flange disposed on the second end of said shaft; and
    a fastener having a male threaded portion adapted for being threaded into the female threaded portion of said shaft,
    wherein the external surface of said shaft is treated to provide a bony in-growth or bony through-growth property thereto.

9. The implant of claim 8, wherein the non-circular cross section is chosen from triangular, square, rectangular, and oval shapes.

10. The implant of claim 8, wherein said shaft comprises titanium.

11. The implant of claim 8, wherein said flange is affixed to said shaft.

12. The implant of claim 8, wherein said flange is integrally formed with said shaft.

13. The implant of claim 8, further comprising a washer having a hole adapted to fit over the threaded portion of said fastener.

14. The implant of claim 8, further comprising means for rotating said fastener into the threaded portion of said shaft.

\* \* \* \* \*